US010286424B2

(12) United States Patent
Stulen et al.

(10) Patent No.: US 10,286,424 B2
(45) Date of Patent: May 14, 2019

(54) ULTRASONIC CLEANING OF SURGICAL INSTRUMENT

(71) Applicant: Ethicon Endo-Surgery, LLC, Guaynabo, PR (US)

(72) Inventors: Foster B. Stulen, Mason, OH (US); Eitan T. Wiener, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 12 days.

(21) Appl. No.: 15/138,677

(22) Filed: Apr. 26, 2016

(65) Prior Publication Data
US 2017/0304876 A1  Oct. 26, 2017

(51) Int. Cl.
| | | |
|---|---|---|
| *B08B 3/12* | (2006.01) | |
| *A61B 17/32* | (2006.01) | |
| *A61B 90/70* | (2016.01) | |
| *A61B 50/20* | (2016.01) | |
| *A61B 50/15* | (2016.01) | |
| *A61B 17/00* | (2006.01) | |

(52) U.S. Cl.
CPC ........ *B08B 3/12* (2013.01); *A61B 17/320068* (2013.01); *A61B 17/320092* (2013.01); *A61B 50/15* (2016.02); *A61B 50/20* (2016.02); *A61B 90/70* (2016.02); *A61B 2017/00504* (2013.01); *A61B 2050/155* (2016.02)

(58) Field of Classification Search
None
See application file for complete search history.

(56) References Cited

U.S. PATENT DOCUMENTS

| | | | |
|---|---|---|---|
| 2,987,068 A | * | 6/1961 | Branson .................... B08B 3/12 134/1 |
| 5,322,055 A | | 6/1994 | Davison et al. |
| 5,324,299 A | | 6/1994 | Davison et al. |
| 5,873,873 A | | 2/1999 | Smith et al. |
| 5,980,510 A | | 11/1999 | Tsonton et al. |

(Continued)

FOREIGN PATENT DOCUMENTS

| | | |
|---|---|---|
| GB | 2 040 150 A | 8/1980 |
| RU | 171617 U1 * | 6/2017 |

OTHER PUBLICATIONS

U.S. Appl. No. 61/410,603, filed Nov. 5, 2010.
International Search Report and Written Opinion dated May 17, 2017 for Application No. PCT/US2017/026414, 12 pgs.

*Primary Examiner* — Rita P Adhlakha
(74) *Attorney, Agent, or Firm* — Frost Brown Todd LLC

(57) ABSTRACT

A cleaning system includes a first container. The first container includes an interior surface and an opening. The interior surface and the opening define a volume. The opening extends along a plane. The interior surface defines at least a portion of a curved surface. The curved surface defines a first focus point. The first focus point is positioned below the plane such that the first focus point is coincident with a portion of the curved surface. The cleaning system further includes a support member and a surgical instrument. The surgical instrument is configured to deliver ultrasonic energy upon activation of the instrument. The surgical instrument comprises an end effector having a distal tip. The support member is configured to support the surgical instrument such that the distal tip is positioned substantially at the first focus point.

19 Claims, 6 Drawing Sheets

(56) References Cited

U.S. PATENT DOCUMENTS

| | | |
|---|---|---|
| 6,056,866 A * | 5/2000 | Maeda .................. A61L 2/035 204/263 |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |
| 6,783,524 B2 | 8/2004 | Anderson et al. |
| 8,057,498 B2 | 11/2011 | Robertson |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 9,901,358 B2 | 2/2018 | Faller et al. |
| 2002/0197182 A1 | 12/2002 | Minter |
| 2003/0191390 A1 | 10/2003 | Murakami |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2013/0068247 A1 | 3/2013 | Batchelor et al. |
| 2015/0080924 A1 | 3/2015 | Stulen et al. |
| 2015/0245850 A1 | 9/2015 | Hibner et al. |

\* cited by examiner

ULTRASONIC CLEANING OF SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
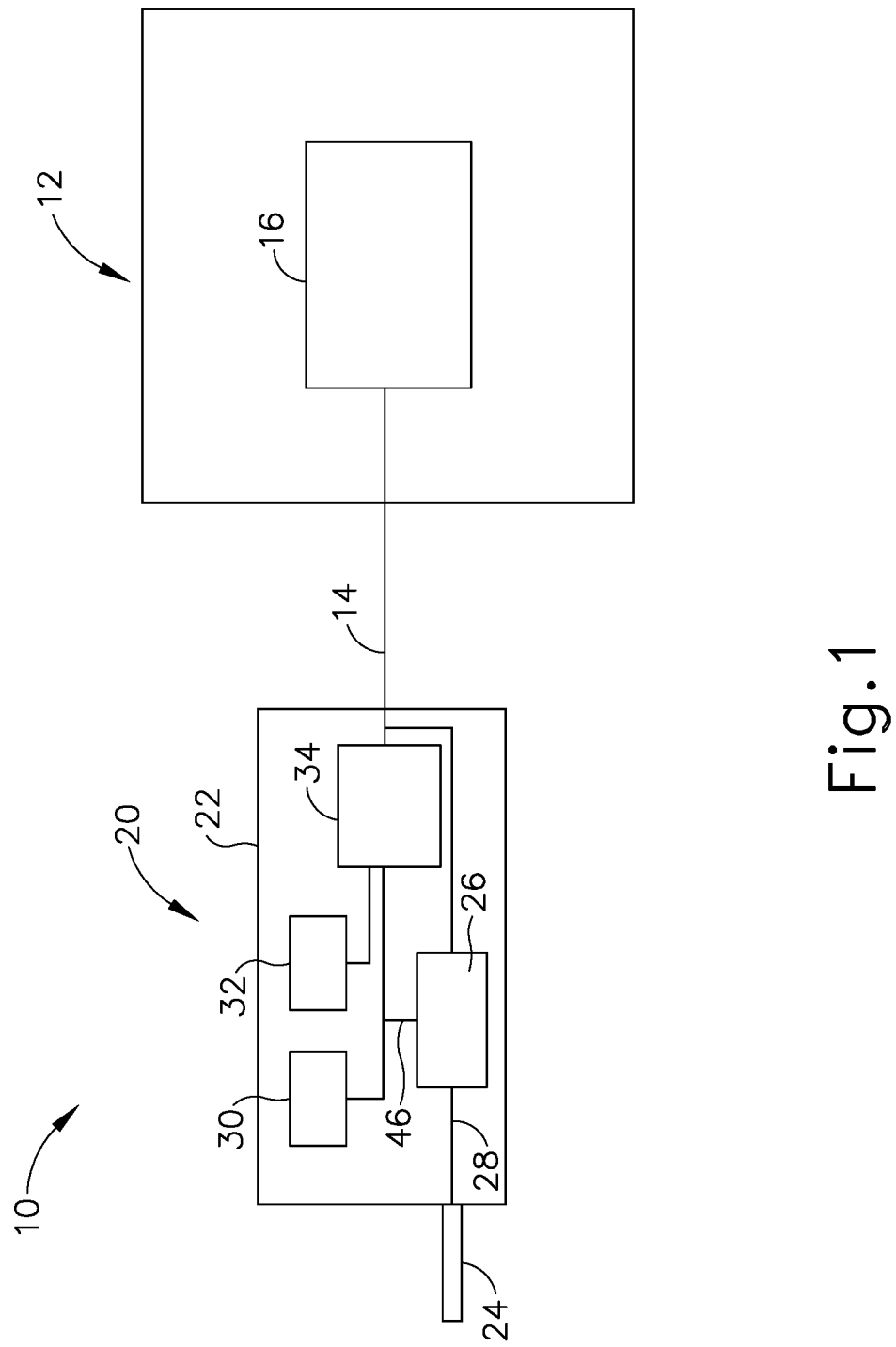
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). Some versions of system (10) may incorporate generator (12) into instrument (20), such that cable (14) may simply be omitted.

By way of example only, generator (12) may comprise the GEN04 or GEN11 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (e.g., via remote control, etc.). In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration.

Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

Those of ordinary skill in the art will understand that, as a matter of physics, the distal end of blade (24) is located at a position corresponding to an anti-node associated with resonant ultrasonic vibrations communicated through waveguide (28) (i.e., at an acoustic anti-node). When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 45 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (110) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
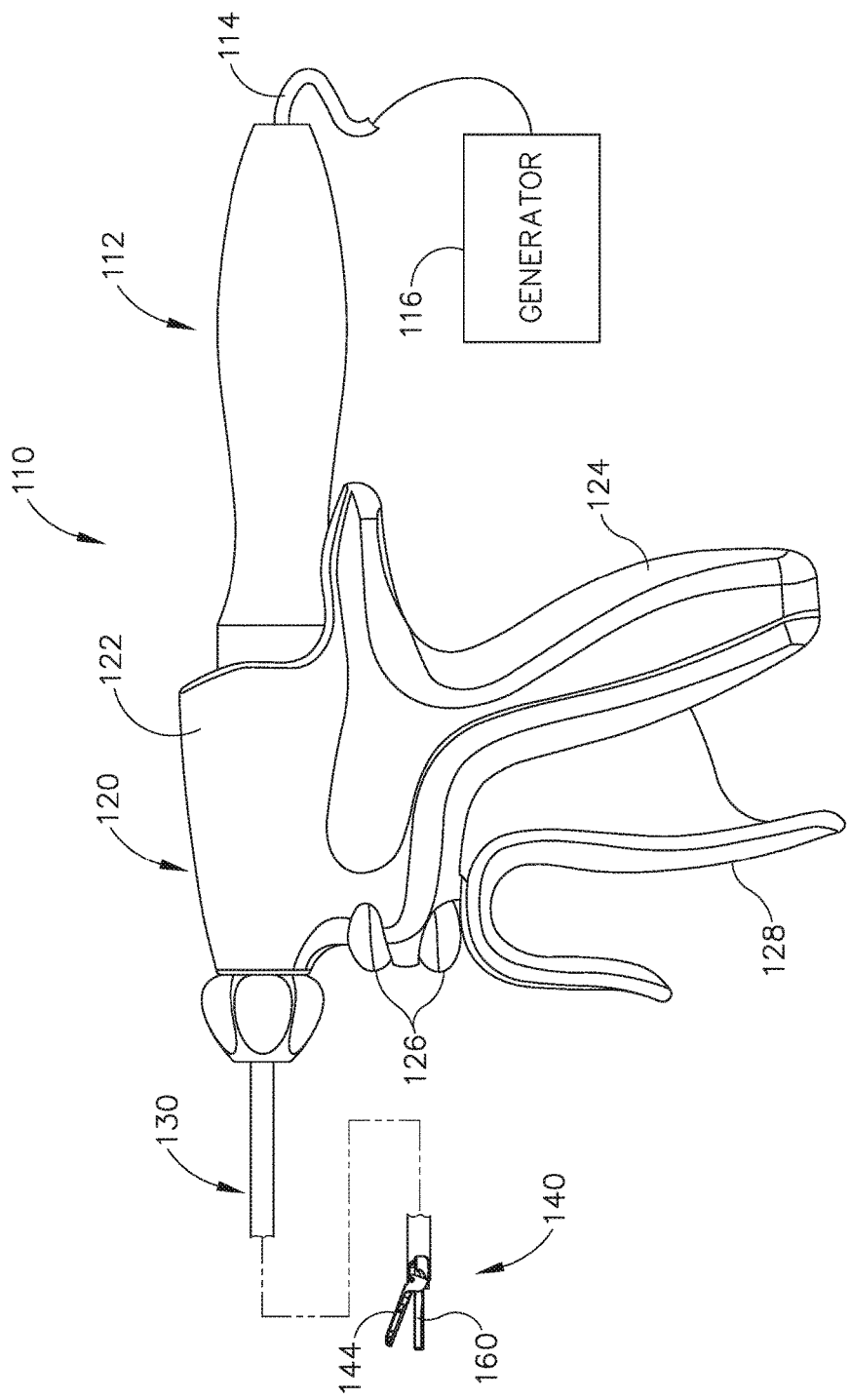
FIG. 2 depicts a side elevational view of an exemplary instrument that may be incorporated into the system of FIG. 1.

FIG. 2 illustrates an exemplary ultrasonic surgical instrument (110). At least part of instrument (110) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, instrument (110) is operable to cut tissue and seal or weld tissue substantially simultaneously.

Instrument (110) of the present example comprises a handle assembly (120), a shaft assembly (130), and an end effector (140). Handle assembly (120) comprises a body (22) including a pistol grip (124) and a pair of buttons (126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Ultrasonic blade (160) may be configured and operable just like ultrasonic blade (24) described above.

Clamp arm (144) is pivotably coupled with an inner tube (133) and an outer tube (132) (FIGS. 3 and 4) that form shaft assembly (130). Such an inner and outer tube configuration may be provided in accordance with the teachings of various references that are cited herein. Clamp arm (144) is further coupled with trigger (128). Trigger (128) is operable to drive one of the tubes of shaft assembly (130) longitudinally while the other tube of shaft assembly (130) remains stationary. This relative longitudinal movement between the tubes of shaft assembly (130) provides pivotal movement of clamp arm (144). Clamp arm (144) is thus pivotable toward ultrasonic blade (160) in response to pivoting of trigger (128) toward pistol grip (124); and clamp arm (144) is pivotable away from ultrasonic blade (160) in response to pivoting of trigger (128) away from pistol grip (124). Clamp arm (144) is thereby operable to cooperate with ultrasonic blade (160) to grasp and release tissue; and clamp arm (144) is further operable to compress tissue against ultrasonic blade (160) to thereby enhance the transfer of ultrasonic energy from ultrasonic blade (160) to the tissue. Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 2.

An ultrasonic transducer assembly (112) extends proximally from body (122) of handle assembly (120). Transducer assembly (112) may be configured and operable just like transducer (26) described above. Transducer assembly (112) is coupled with a generator (116) via a cable (114). It should be understood that transducer assembly (112) receives electrical power from generator (116) and converts that power into ultrasonic vibrations through piezoelectric principles. Generator (116) may be configured and operable like generator (12) described above. Generator (116) may thus include a power source and control module that is configured to provide a power profile to transducer assembly (112) that is particularly suited for the generation of ultrasonic vibrations through transducer assembly (112). It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

As shown in FIG. 2, by way of example, one of the buttons (126) may be associated with a "seal" mode, such that actuating the particular one of the buttons (126) only seals tissue, but does not cut tissue, when the tissue is being clamped between clamp arm (144) and blade (160). In particular, activation of a first one of the buttons (126) may cause vibration of ultrasonic blade (160) at a relatively low amplitude. Similarly, by way of further example, the other of the buttons (126) may be associated with a "cut and seal" mode such that actuating the particular one of the buttons (126) may seal and cut tissue when the tissue is being clamped between clamp arm (44) and blade (160). In particular, activation of a second one of the buttons (126) may cause vibration of ultrasonic blade (160) at a relatively high amplitude. Other suitable operational modes that may be associated with buttons (126) will be apparent to persons skilled in the art in view of the teachings herein.

Figure 3:
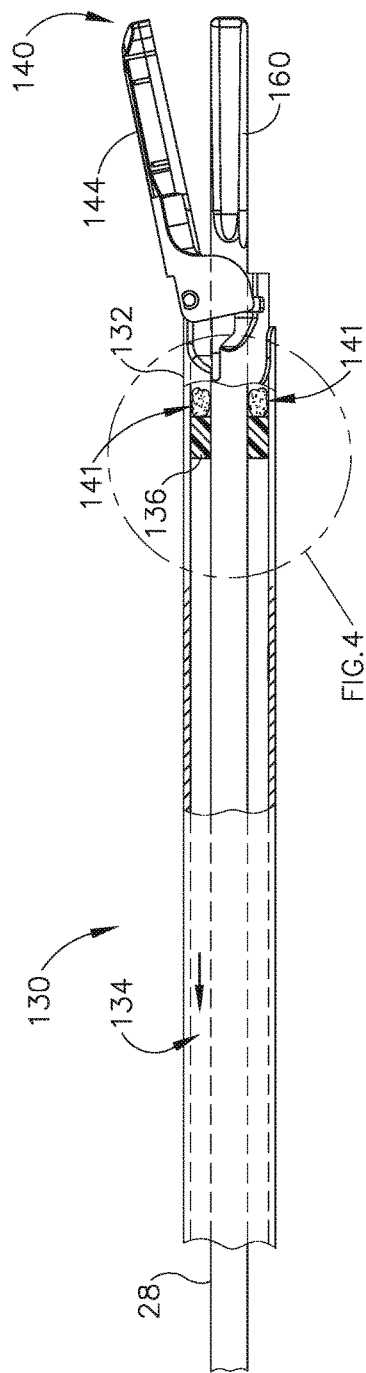
FIG. 3 depicts a partial cross-sectional side view of the shaft assembly of the instrument of FIG. 2.
Figure 4:
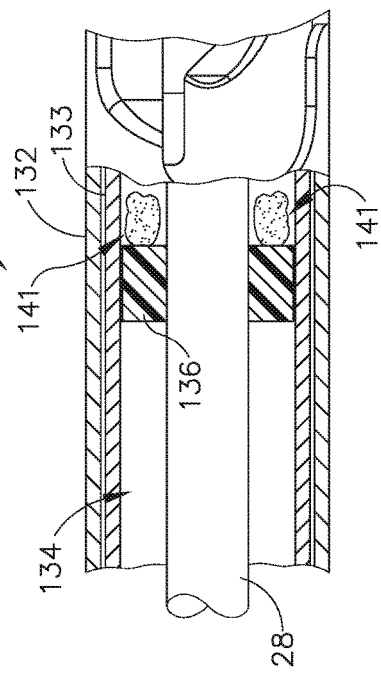
FIG. 4 depicts a detailed cross-sectional side view of a portion of the shaft assembly of the instrument of FIG. 2.

As best seen in FIGS. 3-4, shaft assembly (130) of the present example comprises an outer tube (132) and an inner tube (133). It should be understood that inner tube (133) is omitted from FIG. 3 for clarity. A lumen or gap (134) is defined between the interior of inner tube (133) and the exterior of waveguide (28). Both tubes (132, 133) are pivotably coupled with clamp arm (144) as noted above, such that relative longitudinal movement between tubes (132, 133) will provide pivot movement of clamp arm (144) toward and away from blade (160).

Shaft assembly (130) also includes a distal-most bumper (136) positioned coaxially around waveguide (28) and within inner tube (133). As shown, bumper (136) assists in maintaining the radial position of waveguide (28) within shaft assembly (330), and attenuates vibrations from waveguide (28) to other components of shaft assembly (130). Bumper (136) is located at a longitudinal position along waveguide (28) corresponding to a node associated with ultrasonic vibrations communicated through waveguide (28) (i.e., a location where the vibrational amplitude is minimal). In the present example, bumper (136) comprises an annular member that is sized to provide an interference fit within inner tube (133). However, bumper (136) is slidable within inner tube (133) and may include a lubricious coating to allow for such relative movement. Bumper (136) of the present example comprises an elastomeric material but in other examples may comprise any suitable material. Bumper (136) provides as a fluid barrier between the distal portion of gap (134) and the remaining portions of gap (134) that are proximal to bumper (136), such that bumper (136) essentially seals the proximal portion of gap (134) from a more distal portion of gap (134).

Shaft assembly (130) is configured such that relative longitudinal movement is possible between waveguide (28) and the combination of tubes (132, 133). In some versions, waveguide (28) is configured to translate longitudinally while tubes (132, 133) remain stationary. By way of example only, shaft assembly (130) may provide longitudinal movement of waveguide (28) and blade (160) relative to tubes (132, 133) in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jun. 3, 2018, the disclosure of which is incorporated by reference herein. In some other versions, tubes (132, 333) are configured to translate together longitudinally while waveguide (28) remains stationary. Various suitable ways in which such relationships may be provided will be apparent to those of ordinary skill in the art in view of the teachings herein.

III. Exemplary Cleaning Systems

While instruments such as instrument (110) are effective for cutting and sealing tissue as described above, using energy to treat tissue may result in debris (e.g., tissue particles, coagulated blood, etc.) becoming stuck to end effector (40, 140) and other portions of instrument (110). For example, debris may be forced into portions of shaft assembly (130), particularly into a gap like gap (134) described above, such as debris (141) shown in gap (134) in FIGS. 3 and 4. In some environments, instruments such as instrument (110) may be cleaned, sterilized, and reused. It will be appreciated that the design and structure of such instruments (110) may make it difficult to clean end effector (140) and/or the internal portions of shaft assembly (130). In particular, due to the design and structure of such instruments, debris (141) may tend to remain within shaft assembly (130), for example, even after a conventional cleaning and sterilization processes. Such debris can eventually form a plug just distal to bumper (136), potentially leading to, among other issues, an increased load on generator (116), additional heating at bumper (136), and/or a decreased vibrational output through waveguide (28) and blade (160). It may therefore be desirable to provide a system or apparatus that enables cleaning of portions of instrument (110), such as end effector (140) and portions of shaft assembly (130), that are otherwise difficult to clean. It may also be desirable to provide a system or apparatus that utilizes the ultrasonic energy capabilities of instruments, such as instrument (110), to aid in cleaning such instruments. The following provides examples of exemplary cleaning systems and methods that rely on the ultrasonic energy capabilities of an instrument (110) to clean end effector (140) and a distal portion of shaft assembly (130).

In the present example, it is contemplated that the cleaning systems described below would be used to remove debris from instrument (110) without necessarily sterilizing instrument (110). In other words, instrument (110) may first be processed in one of the cleaning systems described below; and then instrument (110) may subsequently processed in another system in order to sterilize instrument (110). Instrument (110) may also be processed in various other kinds of systems as will be apparent to those of ordinary skill in the art in view of the teachings herein.

A. Cleaning Tank including Energy Reflecting Surface

Figure 5:
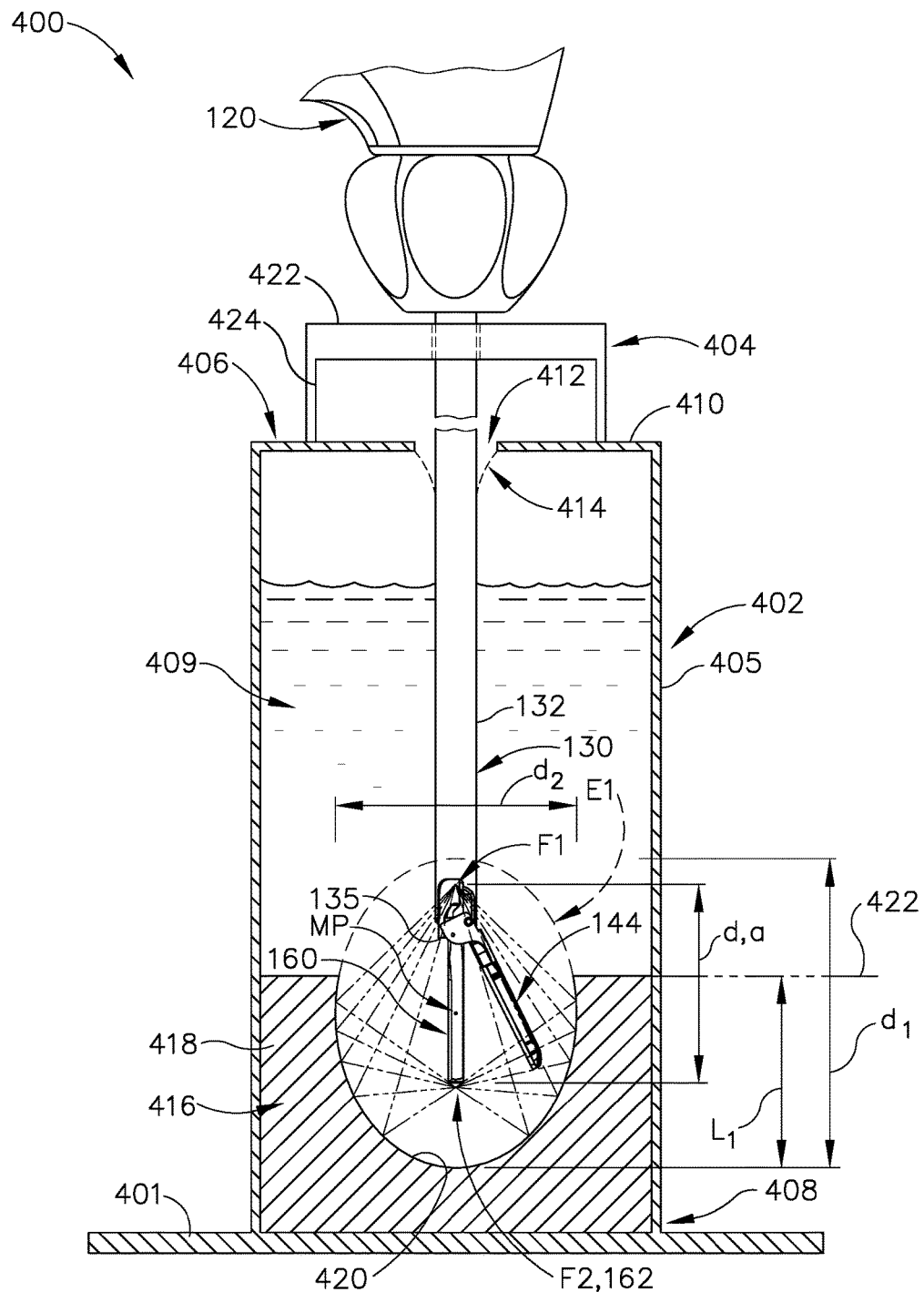
FIG. 5 depicts a partial cross-sectional side view of an exemplary cleaning system suitable for cleaning a distal portion of the instrument of FIG. 2.

FIG. 5 shows an exemplary cleaning system (400). As shown, cleaning system (400) is configured to support instrument (110) such that a portion of shaft assembly (130) and end effector (140) are disposed within a tank (402) of the cleaning system (400). Cleaning system (400) is configured to receive shaft assembly (130) and end effector (140) of instrument (110), and to utilize ultrasonic waves generated by instrument (110) to clean the instrument (110) itself. Particularly, as discussed in further detail below, cleaning system (400) includes features that reflect and focus such ultrasonic waves toward particular components of instrument (110) to aid in cleaning such components. Thus, instrument (110) itself in some examples may be considered part of cleaning system (400). However, in other examples, instrument (110) is not considered to be part of cleaning system (400).

As shown in FIG. 5, cleaning system (400) includes a base (401), tank (402), and support member (404). Tank (402) includes a sidewall (405), an open end (406), and a closed end (408), and therefore defines a volume for receiving a fluid, for example, such as a host cleaning fluid (409). It will be understood that the host cleaning fluid (409) may be added to tank (402) by an operator during or after performing a procedure using instrument (110). As shown, fluid (409) comprises saline (which may be commonly found in an operating room), but may comprise any liquid suitable for aiding in the cleaning of instrument.

In the example shown, tank (402) is cylindrical in shape, but in other examples may be any suitable shape. Open end (406) includes a lid or cover (410), which includes an opening (412) for receiving the shaft assembly of an instrument, such as shaft assembly (130) of instrument (110), for example. Opening (412) includes a valve or seal member (414) that allows for the insertion of shaft assembly (130) into tank (402). Seal (414) is further configured to substantially prevent fluid from escaping out of opening (412) during use of cleaning system (400), due to splashing of the fluid (409), for example. By way of example only, seal (414) may comprise a duckbill valve, an iris seal, and/or any other suitable kind of sealing structure that will allow passage of end effector (140) and shaft assembly (130) into the interior of tank (402) yet seal against the exterior of outer tube (132). When the operator inserts end effector (140) and shaft assembly (130) through seal (414) into tank (402), the operator may hold trigger (128) in a squeezed position toward pistol grip (124), thereby maintaining end effector (140) in a closed configuration (i.e., with clamp arm (144) pivoted toward blade (160)). Once instrument (110) is suitable positioned relative to tank (402), the operator may release trigger (128) and thereby allow end effector (140) to return to an open configuration (i.e., with clamp arm (144) pivoted away from blade (160)).

Cleaning system (400) further includes a reflector (416) positioned within tank (402). Reflector (416) is configured to reflect and focus ultrasonic waves generated by instrument (110) back toward instrument (110). Reflector (416)

defines a body (418) and a reflecting surface (420). In the example shown, reflecting surface (420) comprises a portion of ellipsoid shape (E1) having a major axis with a length $d_1$ and a minor axis with a length $d_2$. The portion of the ellipsoid shape (E1) defining reflecting surface (420) has an effective length $L_1$, which is less than length $d_1$. As will be understood by persons skilled in the art, the ellipsoid shape (E1), a part of which reflecting surface (420) comprises, defines two foci (F1, F2), which are equidistant from the midpoint (MP) where each axis of the ellipsoid shape (E) intersect. It should be understood that the major axis includes both foci (F1, F2). Focus (F1) is positioned above a plane (422) defining the top portion of reflector (416), such that focus (F1) is not coincident with reflecting surface (420); while focus (F2) of ellipsoid (E1) is positioned below plane (422) and is thus coincident with reflecting surface (420). In other examples, the position of top portion of plane (422) may be different than that shown, for example, by increasing or decreasing effective length (L1) of reflecting surface (420). Other suitable configurations of reflector (416) and reflecting surface (420) will be apparent to persons skilled in the art in view of the teachings herein.

As shown, body (418) of reflector (416) is constructed such that it does not vibrate at a predetermined vibratory frequency $f_o$ of, for example, 55.5 kHz, that is the operating frequency of blade (160). In some examples, body (418) includes a sufficient acoustic impedance to resist vibrating as it is subjected to ultrasonic waves, such as ultrasonic waves traveling through host fluid (409) from blade (160), at a predetermined vibratory frequency $f_0$. In such examples, body (418) is made of a material or materials with a particular thickness and/or material structure that provide body (418) with the sufficient acoustic impedance. For example, body (418) may be constructed of a solid mass of metal such as stainless steel. However, in other examples, body (418) may be configured in other manners and of other materials, provided that it includes the sufficient impedance mentioned above. In some examples, body (418) has a higher impedance than the liquid (409) that is contained in tank (402). By way of example only, body (418) of reflector (416) may have an acoustic impedance that is at least 10 times greater than the acoustic impedance of the liquid (409) that is contained in tank (402). In some other versions, body (418) has a lower impedance than the liquid (409) that is contained in tank (402).

In the alternative, body (418) may be constructed such that it includes a mechanical or vibrational resonance that does not fall on the nominal vibrational resonance of the blade (160) as the blade (160) oscillates as discussed herein. In such examples, body (418) may comprise a hollow shell of material or materials. Other suitable configurations and materials that body (418) may comprise in order to prevent mechanical oscillations of reflector (416) and other portions of cleaning system (400) due to ultrasonic waves of blade (160) will be apparent to persons skilled in the art in view of the teachings herein. Similarly, other suitable configurations and material(s) that the reflector (416) may comprise will be apparent to persons skilled in the art in view of the teachings herein. Moreover, while reflecting surface (420) is described herein to define a portion of an ellipsoid shape, reflecting surface (420) in other examples may define a whole or a portion of other types of quadric surfaces, such as a spheroid, sphere, paraboloid, hyperboloid, cone, or cylinder. Other suitable configurations and shapes that reflecting surface (420) may comprise will be apparent to persons skilled in the art in view of the teachings herein.

Support member (404) of the present example is configured to support instrument (110) such that the distal end or tip (162) of blade (160) is positioned substantially at or coincident with focus (F2) and distal end (135) of shaft (132) is positioned substantially at or coincident with focus (F1). Moreover, support member (404) is configured to rigidly hold instrument (110) in order to substantially prevent movement of instrument (110) during oscillations of waveguide (28) and blade (160). In the example shown, support member (404) includes a support platform (422) and support legs (424). As shown, support legs (424) extend from platform (422) to cover (410). As shown, platform (424) is positioned relative to foci (F1, F2) such that when a portion of instrument (110) rests on platform (424), distal end (135) of shaft (132) is positioned substantially at or coincident with focus (F1) and tip (162) of blade (160) is positioned substantially at or coincident with focus (F2). In particular, in the present example, platform (424) is positioned relative to foci points (F1, F2) such that when rotation knob (137) rests on or abuts platform (424), distal end (135) of shaft (132) is positioned substantially at or coincident with focus (F1) and tip (162) of blade (160) is positioned substantially at or coincident with focus point (F2). Thus, the distance between foci (F1, F2) as indicated by distance (a) is substantially equal to the length or distance between distal end (135) of shaft (132) tip (162) of blade (160) (as indicated by distance (d) in FIG. 5.).

In other examples, platform (424) may be positioned and/or configured to support other portions of instrument (110), such as a portion of handle assembly (120). Moreover, while it is discussed herein that distal end (135) of shaft (132) is placed at focus (F1) and tip (162) of blade (160) is positioned at focus (F2), it will be understood that other portions of instrument (110), or no portions of instrument (110), may be positioned at foci (F1, F2), respectively. In some examples, other stops, fiduciaries, or other features in addition, or in the alternative, to support member (404) may be included in order to ensure stabilization and placement of instrument (110). Also in some instances, it may be possible for the operator to observe when the energy is being reflected as instrument (110) is being immersed in liquid (409). For instance, some experienced operators may be able to properly immerse instrument (110) in liquid (409) at the appropriate depth in a "free hand" fashion, such that depth stops or other similar features may not be needed.

Cleaning system (400) may be configured to accommodate a variety of instruments and sizes of instruments. In some examples, support member (424) is adjustable in order to accommodate for shaft assemblies (130) having longer or shorter lengths than that of shaft assembly (130) shown. Specifically, in some examples, support member (424) may be movable toward or away from tank (402) in order to ensure proper alignment with foci (F1, F2) discussed above. It should also be understood that, in some versions of cleaning system (400), different platforms (424) may be provided with different configurations, such that a particular platform (424) may be selected based on the particular length of shaft assembly (130) being used. Such modular platforms (424) may be removably coupled with cover (410) to enable different lengths of shaft assemblies (130) to be appropriately positioned relative to reflecting surface (420). In addition or in the alternative to the foregoing, cleaning system (400) may include a sensor or sensors operable to detect whether tip (162) and/or distal end (135) of shaft (132) are properly positioned, such as at foci (F1, F2), respectively. In examples where support member (424) is configured to provide adjustable spacing, support member (424) may communicate with the position sensor(s) and automatically adjust the position of shaft assembly (130) according to positioning feedback from the sensor(s).

In addition or in the alternative, different reflectors (416) may be provided in order to accommodate for instruments with different distances (d) between tip (162) and distal end (135) of shaft (132). For example, where (d) does is not substantially equal to the distance (a) between foci (F1, F2), it may be desired to adjust the distance between foci (F1, F2) to equal such distance (d). In such instances, reflector (416) may be interchangeable with a variety different reflectors (416) having a different distance (a) between foci (F1, F2) corresponding with a variety of instruments having particular lengths (d). In such instances, an entire cleaning system (400) having a different reflector with a distance (a) according to the length (d) of instrument may be provided. Alternatively, tanks (402) having such varying reflectors (416) may be provided. Further alternatively, reflector (416) may be removed from tank (402) and replaced with different reflectors (416) defining various distances between foci (F1, F2). Other suitable configurations of reflector (416) will be apparent to persons skilled in the art in view of the teachings herein.

In addition or in the alternative, instruments having adjustable shafts (132) may be provided so that distance (d) between tip (162) and distal end (135) of shaft (132) may be adjusted so that it substantially equals the distance (a) between foci (F1, F2). For example, instrument (110) may be provided with a shaft (132) that may move axially relative to blade (160) such that distal end (135) of shaft (132) may be aligned with focus (F2).

Figure 6:
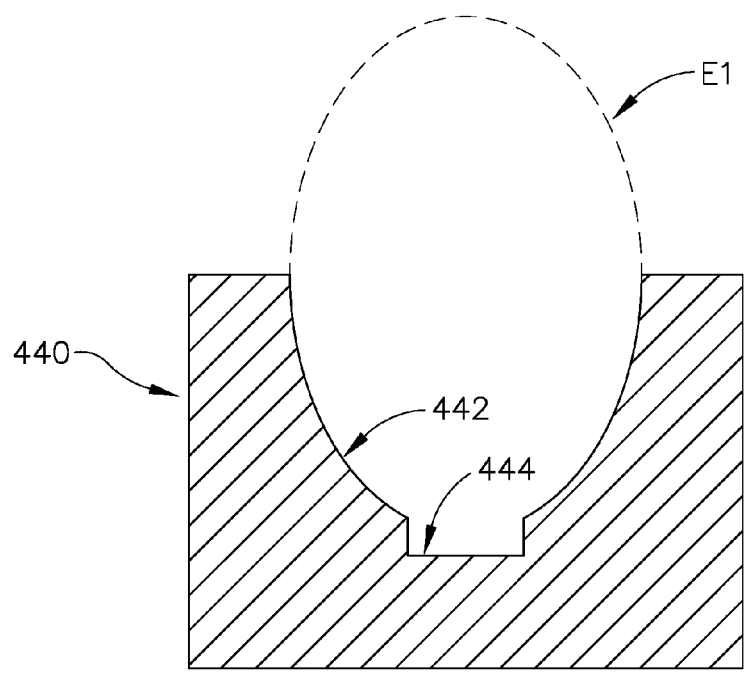
FIG. 6 depicts a cross-sectional side view of an exemplary alternative reflector that is suitable for incorporation into the cleaning system of FIG. 5.

An alternative reflector (440) is shown in FIG. 6. Reflector (440) may be incorporated into a cleaning system, such as cleaning system (400) described above, in place of reflector (416). Moreover, reflector (440) may be readily incorporated into the stand (500) described below. In the example shown, reflector (440) is similar to reflector (416), such that it includes a reflecting surface (442) comprising a portion of ellipsoid shape (E1), like reflector (416). However, reflecting surface (442) has a significant structural difference with reflecting surface (420). In particular, reflector (440) of the present example includes a cylindraceous recess (444) at a bottom portion thereof. Thus, in addition to providing the reflection of ultrasonic waves as described with respect to reflector (416), cylindraceous recess (444) increases the reflection of transverse vibration and thus extends the region of vibrations and thus the region of cleaning of instrument (110). In some alternative versions, the sidewalls of recess (444) have a parabolic curvature.

The configuration of reflector (440) may be desirable for versions of instrument (110) where blade (160) provides transverse vibration at a location that is proximal to distal tip (162) of blade (160) (e.g., approximately 5 mm to 10 mm proximal to distal tip (162)). It may be more effective to have this transversely vibrating region of blade (160) at focus (F2), rather than having distal tip (162) at focus (F2). The configuration of cylindraceous recess (444) may thus place the location of focus (F2) at the transversely vibrating region of blade (160). It should be understood that, even in versions of blade (160) where some region proximal to tip (162) provides transverse vibrational motion, tip (162) may still be vibrating as well. It should also be understood that the configuration of cylindraceous recess (444) may still reflect the vibrational energy from tip (162) back toward distal end (135) of shaft (132).

Continuing with the example of a blade (160) that provides transverse vibrational motion at some region proximal to tip (162), some such instruments (110) may be configured such that blade (160) provides a longitudinal vibrational motion at a first frequency; and a transverse vibrational motion at a second frequency. Instrument (110) may enable the operator to select which frequency to use. By way of example only, the first frequency may be selected when blade (160) will be operating on tissue; while the second frequency may be selected when the operator wishes to clean blade (160) in fluid contained in reflector (440).

B. Surgical Stand Including Cleaning Well Having Energy Reflecting Surface

Figure 8:
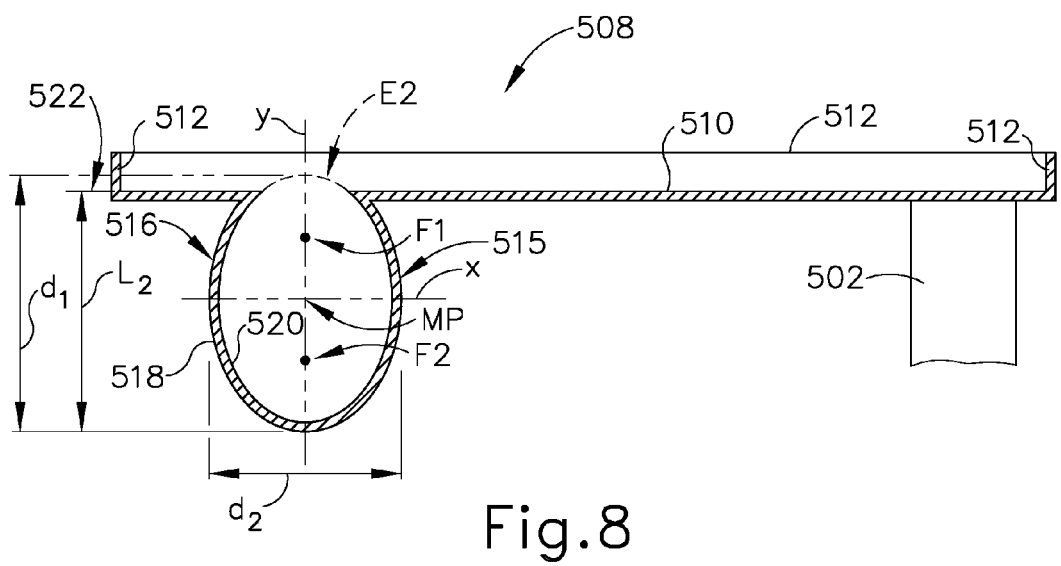
FIG. 8 depicts a cross-sectional view of a tray of the medical stand of FIG. 7, taken along line 8-8 of FIG. 7.
Figure 7:
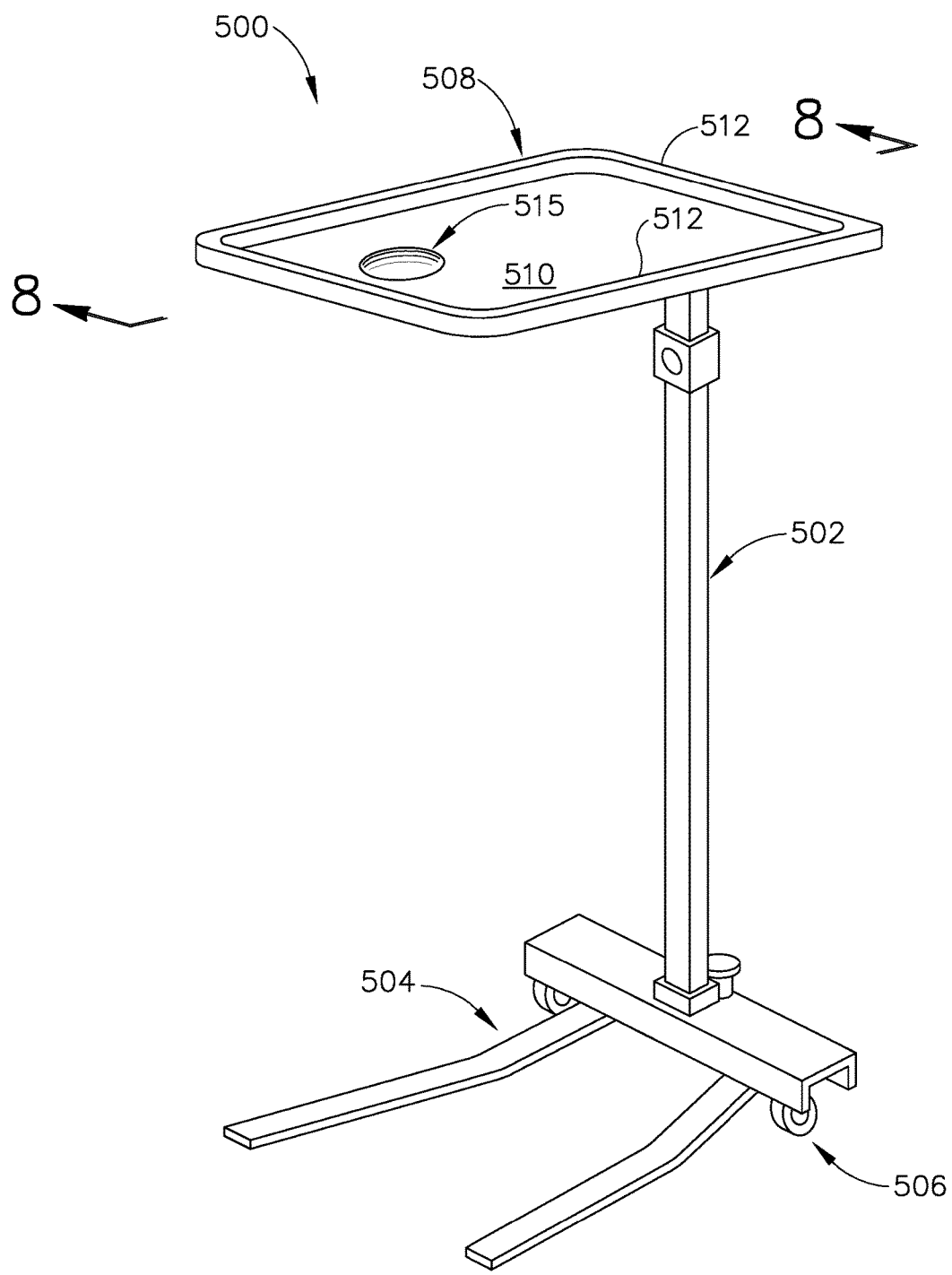
FIG. 7 depicts a perspective view of an exemplary medical stand, including an integral reflector.

In another alternative example, an alternative reflector (516) may be positioned on a medical stand (500), such as on a stand known in the art as a mayo stand as shown in FIGS. 7 and 8. Stand (500) is movable and such that stand (500) may be positioned over or adjacent to a surgical site. In the example shown, stand (500) includes a support rod (502), support legs (504), and wheels (506). Support rod (502) is adjustable such that the height of stand (500) is adjustable. Stand (500) further includes a tray (508) defining a tray surface (510) and a plurality of sidewalls (512).

Stand (500) further includes a cleaning well (515) that is configured to receive a volume of cleaning fluid. Well (515) defines a reflector (516) that is configured to reflect and focus ultrasonic waves generated by instrument (110) toward instrument (110) when instrument is placed properly relative to reflector (516), in a manner similar to reflector (416) as shown in FIG. 5. In the example shown in FIGS. 7-8, reflector (516) defines a body (518) and a reflecting surface (520). Reflecting surface (520) comprises a portion of ellipsoid shape (E2) having a major axis with a length $d_1$ and a minor axis with a length $d_2$. As will be understood by persons skilled in the art, the ellipsoid shape (E2), a part of which reflecting surface (520) comprises, defines two foci (F1, F2), which are equidistant from the midpoint (MP) where each axis (x, y) of the ellipsoid shape (E2) intersect. In this example, reflecting surface (520) comprises more of an ellipsoid shape than reflecting surface (420). Also in this example, assuming the major and minor axes of ellipsoid (E1) have the same length as those of ellipsoid (E2), respectively, reflecting surface (520) includes a larger surface area than reflecting surface (420). Moreover, the effective length (L2) of ellipsoid (E2) is longer than the effective length (L1) of ellipsoid (E1).

Unlike cleaning system (400), which includes a tank (402) and is configured to contain a volume of fluid substantially above reflector (416), stand (500) is only configured to hold a volume of fluid within reflector (516) up to tray surface (510). Thus, as shown, reflector (516) of the present example is configured such that both foci (F1, F2) of ellipsoid (E2) lie below a plane (522) defined by tray surface (510) and the top portion of well (515). Reflector (516) thus defines a volume for receiving a host cleaning fluid, including, but not limited to, saline. In other examples, however, stand (500) may include a structure, such as a tank, placed in communication with well (515), that increases the effective volume of fluid that well (515) may receive. Other suitable configurations of well (515) reflector (516) and reflecting surface (520) will be apparent to persons skilled in the art in view of the teachings herein.

Reflector (516) is configured to have substantially similar mechanical properties as reflector (416). That is, in the example shown, body (518) of reflector (516) is constructed such that it does not vibrate at a predetermined vibratory frequency $f_o$ of, for example, 55.5 kHz. In some examples, body (518) includes a sufficient acoustic impedance to resist vibrating as it is subjected to ultrasonic waves, such as ultrasonic waves traveling through host fluid (509) from blade (160), at a predetermined vibratory frequency $f_0$. In such examples, body (518) is made of a material or materials with a particular thickness and/or material structure that provide body (518) with the sufficient acoustic impedance. In the example shown, body (518) is constructed from a shell of metal such as stainless steel. As shown, the thickness of body is the same as the thickness of tray of stand (500). However, in other examples, body may be thicker or thinner than tray (508) of stand (500). For example, body (518) may be constructed of a solid mass of metal such as stainless steel similar to body (418), for example. However, in other examples, body (518) may be configured in other manners and of other materials, provided that it includes the sufficient impedance mentioned above. In some examples, body (518) includes a higher impedance than the cleaning liquid that is contained in well (515). However, in other examples, body (518) may include a lower impedance than the liquid that is contained in well (515).

In the alternative, body (518) may be constructed such that it includes a mechanical or vibrational resonance that does not fall on the nominal vibrational resonance of the blade (160) as the blade (160) oscillates as discussed herein. Additionally or alternatively, body (518) may be porous or of another configuration that provides such vibrational resistance. Other suitable configurations and materials that body (518) may comprise in order to prevent mechanical oscillations of reflector (516) and other portions of stand (500) due to ultrasonic waves of blade (160) will be apparent to persons skilled in the art in view of the teachings herein. Similarly, other suitable configurations and material(s) that the reflector (516) may comprise will be apparent to persons skilled in the art in view of the teachings herein. Moreover, while reflecting surface (520) is described herein to define a portion of an ellipsoid shape, reflecting surface (520) in other examples may define a whole or a portion of other quadric surfaces, such as a spheroid, sphere, paraboloid, hyperboloid, cone, or cylinder. Other suitable configurations and other suitable shapes that reflecting surface (520) may comprise will be apparent to persons skilled in the art in view of the teachings herein.

In some examples, one or more support members (e.g., like support member (404)), stops, fiduciaries, and/or other features may be included with stand (500) in order to ensure stabilization and proper placement of instrument (110) relative to reflector (516) in a manner similar to that described above. For example, such features may be provided in order to ensure that distal end (135) of shaft (132) is positioned substantially at or coincident with focus (F1) and tip (162) of blade (160) is positioned substantially at or coincident with focus point (F2) of ellipsoid (E2), for example. Other suitable manners of properly positioning instrument (110) relative to reflecting surface (520) will be apparent to persons skilled in the art in view of the teachings herein. It should also be understood that a sealing member (e.g., similar to seal member (414) described above) may be positioned at the top of well (515) to assist in containing cleaning fluid within well (515).

IV. Exemplary Operation

The following describes an exemplary use of system (400) or stand (500), in which an operator would utilize system (400) or stand (500) to clean instrument (110). It should be understood that the following acts may take place before instrument (110) is sterilized. In other words, the following acts may be performed simply to clean instrument (110); such that instrument (110) may be subsequently processed in a sterilization system in order to sterilize instrument (110). Various suitable sterilization systems and techniques will be apparent to those of ordinary skill in the art in view of the teachings herein.

In an exemplary use, an operator places instrument (110) and ensures proper placement of instrument (110) relative to reflecting surface (420, 442, 520), such as in one of the manners discussed above. The operator then activates instrument (110) using a drive signal from generator (116), thus generating mechanical oscillations in transducer (112) and transferring those oscillations to waveguide (28) to reach blade (160), thereby providing oscillation of blade (160) at the resonant ultrasonic frequency. The ultrasonic waves propagating from tip (162) of blade (160) will travel through fluid (409). Ultrasonic waves propagating from a source placed at one focus (i.e., focus (F2)) will reflect off of reflecting surface (420, 442, 520) and travel toward the other focus (i.e., focus (F1)). This is due in part to the fact that the sum of the distances from each of the foci (F1, F2) to the same point on the ellipsoid reflecting surface (420, 442, 520) is constant. Thus, the sum of the distances traveled by an ultrasonic wave from one focus to reflecting surface (420, 442, 520), and then from reflecting surface (420, 442, 520) (i.e., after reflection) to the other focus is constant.

Ultrasonic waves propagating from distal tip (162) of blade (160) (due to its position at focus (F2)) may therefore reflect off of any point of reflecting surface (420, 442, 520) and enter distal end (135) of shaft (132) which is positioned at focus (F1). In the present example, such ultrasonic waves reflecting off of reflecting surface (420, 442, 520) will arrive in phase (i.e., reinforced) at the other focus (i.e., focus (F1)). The ultrasonic waves will then enter gap (134) and the luminal space between shafts (132, 133). Because bumper (136) is located at a position corresponding to a node associated with resonant ultrasonic vibrations communicated through waveguide (28), the energy propagating from distal tip may be concentrated, once reflected off of reflecting surface (420, 442, 520), at bumper (136) where debris (e.g., tissue particles, coagulated blood, etc.) may reside. The focused energy may thus break apart the residue and thereby enable the residue to be cleared from the gap (134) and/or the luminal space between shafts (132, 133). It should be understood that the intensity of the energy may be sufficient to penetrate shafts (132, 133) and cause high ultrasonic pressures and cavitation at the region occupied by the debris/residue.

As discussed below, instrument (110) may be operated in longitudinal and transverse modes to provide oscillation of blade (160) in either longitudinal and/or transverse modes. For example, blade (160) may be oscillated along a longitudinal direction (i.e., along or parallel to longitudinal axis of instrument (110)), a transverse direction (i.e., transverse to longitudinal axis of instrument (110)), or a combination thereof. Varying the oscillations of blade (160) during a cleaning cycle may allow the operator to vary the directions in which ultrasonic waves are propagated through fluid toward reflecting surface (420, 442, 520), and thereby increase the overall effective cleaning area.

Thus, cleaning of instrument (110) takes place in several respects. First, the friction of the longitudinally oscillating blade (160) within the vibrating liquid (409) cleans waveguide (28) and blade (160). Moreover, the friction due to vibrating liquid (409) cleans the clamp arm (144) and the shaft (132). Finally, the ultrasonic waves propagating into gap (134) and luminal space between shafts (132, 133) clean such lumens, as well as waveguide (28), and bumper (136).

In the example shown, generator (116) may be operated in a cleaning mode or combination of cleaning modes in order to clean instrument (110). For example, one of the cleaning modes may comprise generator (116) providing an output of a continuous drive signal for a predetermined amount of time. In such an example, blade (160) may be driven at a frequency of 55 kHz. Additionally or alternatively, generator (116) may be operated at levels 1 through 5 as discussed above; or at levels below or above such levels during a cleaning mode. An additional or alternative cleaning mode includes operating generator (116) with pulsed drive signals. In such a cleaning mode, the pulsed drive signals may include alternating the voltage and/or current of the applied signal to between zero and a predetermined value, to thereby pulse the longitudinal amplitude of the acoustic assembly signal between zero and a predetermined amplitude. In the pulse mode the peak vibration amplitude of blade (160) can be higher than the highest normal operating amplitude of blade (160) (e.g., higher than "Level 5" referred to above), for example 10 to 20% higher. This is because blade (160) is generating less internal heat since the power is not always on and the liquid (409) absorbs the heat, so the temperature of blade (160) is much less than in normal operation.

Another additional or alternative cleaning mode may include sweep driving, or shifting the frequency of the drive signal from generator (116) up and down around the resonant frequency. In addition or in the alternative, generator (116) may provide an output that causes instrument (110) to be operated in longitudinal mode, a transverse mode, or a combination thereof. In such examples, generator (116) may provide an output that causes longitudinal oscillation of blade (160), transverse oscillation of blade (160), or a combination thereof. For example, generator (116) may be operated to provide both longitudinal and transverse modes of operation of instrument (110). In some such examples, generator (116) may provide a drive signal that results in switching, or sweep driving, between longitudinal and mechanical oscillations. Other suitable cleaning modes that may be utilized to clean instrument (110) will be apparent to persons skilled in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A cleaning system, comprising: (a) a first container, comprising: (i) an interior surface, (ii) an opening, wherein the interior surface and the opening define a volume, wherein the opening extends along a plane, wherein the interior surface defines at least a portion of a curved surface, wherein the curved surface defines a first focus point, wherein the first focus point is positioned below the plane such that the first focus point is coincident with a portion of the curved surface; (b) a support member; and (c) a surgical instrument, wherein the surgical instrument is configured to deliver ultrasonic energy upon activation of the instrument, wherein the surgical instrument comprises an end effector having a distal tip, wherein the support member is configured to support the surgical instrument such that the distal tip is positioned substantially at the first focus point.

Example 2

The cleaning system of Example 1, wherein the curved surface comprises a quadric surface.

Example 3

The cleaning system of any one or more of Examples 1 through 2, wherein the curved surface comprises an ellipsoidal curvature.

Example 4

The cleaning system of any one or more of Examples 1 through 3, wherein the curved surface comprises a parabolic curvature.

Example 5

The cleaning system of any one or more of Examples 1 through 4, wherein the curved surface further defines a second focus point, wherein the second focus point is positioned above the plane.

Example 6

The cleaning system of any one or more of Examples 1 through 4, wherein the curved surface further defines a second focus point, wherein the second focus point is positioned below the plane.

Example 7

The cleaning system of any one or more of Examples 1 through 6, further comprising a second container, wherein the first container is positioned within the second container.

Example 8

The cleaning system of any one or more of Examples 1 through 7, wherein the second container comprises: (i) an open end, (ii) a closed end, and (iii) at least one sidewall extending between the open and closed ends.

Example 9

The cleaning system of Example 8, wherein the cleaning system further comprises an instrument support member at the open end, wherein the instrument support member is configured to position a portion of a surgical instrument relative to the first focus point.

Example 10

The cleaning system of Example 9, wherein the support member is adjustable in order to align a portion of a surgical instrument with the first focus point.

Example 11

The cleaning system of any one or more of Examples 1 through 10, wherein the surgical instrument comprises a shaft assembly, wherein the shaft assembly comprises a distal end, wherein the curved surface defines a second focus point, wherein the cleaning system is configured to support the surgical instrument such that the distal end of the shaft assembly is positioned substantially at the second focus point.

Example 12

The cleaning system of any one or more of Examples 1 through 11, the first container is positioned on or in a medical stand, wherein the plane extends along a tray portion of the medical stand.

Example 13

The cleaning system of claim 12, wherein the curved surface comprises an ellipsoidal curvature defining a portion of an ellipsoid, wherein the tray portion extends parallel to a minor axis of the ellipsoid.

Example 14

The cleaning system of Example 12, wherein the curved surface comprises an ellipsoidal curvature defining a portion of an ellipsoid, wherein an effective width of the opening is shorter than a length of a minor axis of the ellipsoid.

Example 15

The cleaning system of any one or more of Examples 1 through 14, wherein the first container includes a recess at a bottom portion of the first container.

Example 16

The cleaning system of Example 15, wherein the curved surface comprises an ellipsoidal curvature, wherein the recess comprises a parabolic curvature.

Example 17

A method of cleaning a surgical instrument using a cleaning system and ultrasonic energy from the surgical instrument, wherein the cleaning system comprises a first container containing a fluid, wherein the first container defines a reflecting portion, wherein at least a portion of the reflecting portion defines a curved surface, wherein the curved surface defines a first focus point, wherein the surgical instrument comprises an end effector configured to deliver ultrasonic energy upon activation of the instrument, the method comprising: (a) aligning a first portion of the surgical instrument with the first focus point; (b) activating the surgical instrument, thereby delivering ultrasonic energy through the fluid; and (c) reflecting the ultrasonic energy off of the reflecting portion and toward a second portion of the instrument.

Example 18

The method of Example 17, wherein the curved surface further defines a second focus point, wherein the method further comprises aligning the second portion of the instrument with the second focus point.

Example 19

A method of cleaning a surgical instrument using a cleaning system and ultrasonic energy from the surgical instrument, wherein the cleaning system comprises a first container containing a fluid, wherein the first container defines a reflecting portion, wherein at least a portion of the reflecting portion defines a curved surface, wherein the curved surface defines a first focus point, wherein the surgical instrument comprises an end effector and a shaft, wherein the end effector is configured to deliver ultrasonic energy upon activation of the instrument, the method comprising: (a) immersing at least a distal portion of the shaft and the end effector in the fluid; (b) aligning the end effector with the first focus point; and (c) activating the end effector, resulting in reflection of ultrasonic energy from the end effector off of the reflecting surface and toward the distal portion of the shaft.

Example 20

The method of Example 19, wherein the curved surface defines a second focus point, wherein the method further comprises aligning the distal end of the shaft with the second focus point.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A cleaning system, comprising:
   (a) a first container, comprising:
      (i) an interior surface,
      (ii) an opening, wherein the interior surface and the opening define a volume, wherein the opening extends along a proximal plane, wherein the interior surface defines a curved surface extending down from the proximal plane to a distal plane such that the curved surface terminates proximally at the proximal plane and such that the curved surface terminates distally at the distal plane along a concave floor, wherein the distal plane is aligned oppositely from the proximal plane such that the volume is defined between the distal and proximal planes, wherein the curved surface defines a first focus point, wherein the first focus point is positioned below the proximal plane;
   (b) a support member; and
   (c) a surgical instrument, wherein the surgical instrument is configured to deliver ultrasonic energy upon activation of the surgical instrument, wherein the surgical instrument comprises:
      (i) a shaft having a distal end, and
      (ii) an end effector extending distally from the distal end of the shaft, the end effector having a distal tip, wherein the support member is configured to support the surgical instrument such that the distal tip is positioned substantially at the first focus point;
   wherein the curved surface is configured to reflect ultrasonic vibrations generated at the distal tip of the end effector back toward the distal end of the shaft and focus the reflected ultrasonic vibrations at the distal end of the shaft.

2. The cleaning system of claim 1, wherein the curved surface comprises a quadric surface.

3. The cleaning system of claim 1, wherein the curved surface comprises an ellipsoidal curvature.

4. The cleaning system of claim 1, wherein the curved surface comprises a parabolic curvature.

5. The cleaning system of claim 1, wherein the curved surface further defines a second focus point, wherein the second focus point is positioned above the proximal plane.

6. The cleaning system of claim 1, wherein the curved surface further defines a second focus point, wherein the second focus point is positioned below the proximal plane, wherein support member is further configured to position the distal end of the shaft at the second focus point.

7. The cleaning system of claim 6, wherein the curved surface forms part of an ellipsoid, wherein the ellipsoid has a major axis passing through the first focus point and the second focus point.

8. The cleaning system of claim 1, wherein the support member is adjustable in order to align the distal tip of the end effector with the first focus point.

9. The cleaning system of claim 1, the first container is positioned on or in a medical stand, wherein the plane extends along a tray portion of the medical stand.

10. The cleaning system of claim 9, wherein the curved surface comprises an ellipsoidal curvature defining a portion of an ellipsoid, wherein the tray portion extends parallel to a minor axis of the ellipsoid.

11. The cleaning system of claim 9, wherein the curved surface comprises an ellipsoidal curvature defining a portion of an ellipsoid, wherein an effective width of the opening is shorter than a length of a minor axis of the ellipsoid.

12. The cleaning system of claim 1, wherein the first container includes a recess at a bottom portion of the first container.

13. The cleaning system of claim 12, wherein the curved surface comprises an ellipsoidal curvature, wherein the recess comprises a parabolic curvature.

14. The cleaning system of claim 1, further comprising a tank, wherein the first container is positioned in a bottom region of the tank, wherein the tank is configured to contain a fluid, wherein the first container is configured to receive the fluid.

15. The cleaning system of claim 14, wherein the curved surface further defines a second focus point, wherein the second focus point is positioned in the tank above the proximal plane.

16. The cleaning system of claim 14, wherein support member is configured to support the surgical instrument such that the distal end of the shaft is positioned in the tank above the proximal plane.

17. A cleaning system, comprising:
(a) a first container, comprising:
   (i) a non-cylindrical interior surface, wherein the interior surface includes a proximal end and a distal end that together define a volume,
   (ii) an opening, wherein the opening is positioned at the proximal end, wherein the interior surface includes a curved surface extending from the proximal end to the distal end such that the curved surface is longitudinally aligned with the opening, such that the curved surface terminates proximally at the proximal end, and such that the curved surface terminates distally at the distal end, wherein the curved surface defines a first focus point positioned distal to the proximal end and proximal to the distal end;
(b) a support member; and
(c) a surgical instrument, wherein the surgical instrument is configured to deliver ultrasonic energy upon activation of the surgical instrument,
   wherein the surgical instrument comprises:
   (i) a shaft assembly having a distal end, and
   (ii) an end effector extending distally from the shaft assembly, wherein the end effector includes an ultrasonic blade having a distal tip, wherein the support member is configured to support the surgical instrument such that the distal tip is positioned substantially at the first focus point;
   wherein the curved surface is configured to reflect ultrasonic vibrations generated by the ultrasonic blade, wherein the curved surface is further configured to focus the reflected ultrasonic vibrations at the distal end of the shaft assembly.

18. A cleaning system, comprising:
(a) a first container, comprising:
   (i) an interior surface,
   (ii) an opening, wherein the interior surface and the opening define a volume, wherein the opening extends along a plane, wherein the interior surface defines a curved surface having an ellipsoidal curvature, wherein the curved surface and the volume extend distally from the plane, wherein the ellipsoidal curvature defines a first focus point that is distal to the plane, a second focus point proximal to the first focus point, and a major axis extending between the first and second focus points;
(b) a support member, wherein the support member extends proximally from the plane; and
(c) a surgical instrument, wherein the surgical instrument is configured to deliver ultrasonic energy upon activation of the surgical instrument,
   wherein the surgical instrument comprises:
   (i) a shaft assembly having a distal end, and
   (ii) an end effector extending distally from the distal end of the shaft assembly, the end effector having a distal tip, wherein the support member is configured to support the surgical instrument such that the distal tip is positioned substantially at the first focus point and such that the distal end of the shaft assembly is positioned at the second focus point;
   wherein the curved surface is configured to reflect ultrasonic vibrations generated at the distal tip of the end effector and focus the reflected ultrasonic vibrations at the distal end of the shaft assembly based on the respective positioning of the distal tip at the first focus point and the distal end at the second focus point.

19. The cleaning system of claim 18, wherein the support member is removably coupled to the first container at the plane.

* * * * *